US00PP09062P

United States Patent [19]

Olesen et al.

[11] Patent Number: Plant 9,062

[45] Date of Patent: Feb. 28, 1995

[54] SHRUB ROSE PLANT NAMED POULSKOV

[75] Inventors: Mogens Olesen; Pernille Olesen, both of Fredensborg, Denmark

[73] Assignee: Weeks Wholesale Rose Grower, Inc., Upland, Calif.

[21] Appl. No.: 195,769

[22] Filed: Feb. 10, 1994

[51] Int. Cl.[6] ..... A01H 5/00

[52] U.S. Cl. ..... Plt./1

[58] Field of Search ..... Plt. 1, 26

*Primary Examiner*—Howard J. Locker

*Attorney, Agent, or Firm*—Christie, Parker & Hale

[57] ABSTRACT

A new variety of shrub rose suitable for garden decoration, having flowers of soft pink coloration.

1 Drawing Sheet

BACKGROUND OF THE INVENTION

This invention relates to a new and distinct variety of shrub rose. The varietal denomination of the new variety is 'Poulskov'. The plant is a dwarf bushy compact seedling cultivated for outdoor garden decoration and is hardy. 'Poulskov' has as its seed parent an unnamed seedling and as its pollen parent the variety known as 'Egeskov'.

SUMMARY OF THE INVENTION

Among the features which distinguish the new variety 'Poulskov' from other presently availabel and known commercial rose cultivars are the following combination of characteristics: its light pink flowers with consistent quartered form, its nearly continual production of blooms, its very compact rounded habit, its high degree of disease resistance, and its changing peduncle colors that lighten as the bloom matures. 'Poulskov' may be propagated by cuttings, budding, grafting, layering and tissue culture.

Asexual propagation of hte new variety as performed by budding in Kern County and Upland, Calif. shows that the foregoing and other distinguishing characteristics come true to form and are established and transmitted through succeeding propagations.

Comparison with Parent Varieties

The new rose may be distinguished from its seed parent, an unnamed seedling, by the following combination of characteristics: whereas 'Poulskov' bears pink flowers of very full petalation (48 to 62), the seed parent bears white flowers with significantly fewer petals. The new cultivar bears somewhat round foliage with a moderately glossy finish, whereas the seed parent bears more elongated foliage with a matte finish. Whereas the seed parent has an upright moderately tall habit, the habit of 'Poulskov' is significantly shorter and more rounded.

The new variety may be distinguished from its pollen parent, 'Egeskov', by the following combination of characteristic: whereas the new seedling bears flowers of heavy petalation with a moderate apple-like fragrance, the pollen parent bears flowers with significantly less petalage and no distinct fragrance. 'Poulskov' has a short rounded and compact habit, whereas 'Egeskov' has a significantly taller habit.

BRIEF DESCRIPTION OF THE ILLUSTRATION

The accompanying photograph illustrates the plant in color and shows the flowering thereof from bud to full bloom depicted in color as nearly correct as it is possible to make a color illustration of this character. Throughout this specification, color values used are based upon the Colour Chart of The Royal Horticultural Society of London, England, except where common terms of color definition are employed.

DESCRIPTION OF THE NEW VARIETY

The following description is of rose plants of the new cultivar grown outdoors in October 1993 in Upland, Calif. Phenotypic expression may vary with environmental, cultural and climatic conditions, as well as differences in conditions of light and soil.

FLOWER

The new variety bears its flowers sometimes singly, usually four to five or more per stem. Flowers are borne in regular rounded clusters on normal to strong, short to medium stems for the class. Outdoors the plant blooms very abundantly and nearly continuously during the growing season. The flowers have a moderately strong apple-like fragrance. Peduncle length is considered average to long for the class and nominally about 3.5 to 4.5 cm.

BUD

The peduncle is of average to long length for the class, of average caliper, and usually erect. It is moderately smooth with some stipitate glands. On the more mature flowers, peduncle color is between 144A and 138A, sometimes very lightly suffused with near 180C. On the younger buds, peduncle color is similar but more heavily suffused with near 180C.

Before the calyx breaks, the bud is of small to medium size for the class, moderately short in length, and pointed to ovoid to slightly globular in shape. The surface of the bud bears very few stipitate glands usually with slender entire foliaceous parts extending beyond the tip of the bud equal to $\frac{1}{4}$ or more of its length. Bud color is between 144A and 138A.

The inner surface of the sepals is coverd with fine wooly tomentum; sepal margins are lined with numerous hair.

As the first petal opens, the bud is small to medium for the class, moderately short in length, and somewhat pointed to ovoid to slightly globular in form. Overall bud size is considered small to medium and moderately short; nominally about 2 to 2.5 cm in length and about 1.5 to 2 cm in diameter at its widest point. The color of the undersurfaces of the newly opened petals is between 55D and 56A with a basal attachment zone of between 154D and 4D. The color of the upper surfaces of the newly opened petals is between 49C and 55D with a basal attachment zone of between 154D and 4D. The bud opens up well and is not prevented from opening by wet, cold, hot or dry weather.

BLOOM

When fully open, the bloom is somewhat small to medium for the class, ranging from 6 to 8 cm in diameter. Petalage is very double with 48 to 62 petals and numerous petaloids arranged irregularly. When partially open, the bloom form is very cupped to full and the petals are moderately tightly spiraled to cupped with petal edges somewhat rolled outward. When fully open, the bloom form is very quartered to globular, and the petals are moderately cupped with petal edges moderately rolled to quilled outward.

PETALS

The petals are of moderately heavy substance and of medium thickness, with upper surfaces slightly satiny and undersurfaces slightly shiny to satiny. The outer petals are nearly round to broadly obovate in shape with apices usually rounded and sometimes slightly notched with one or more notches. The inside petals are narrowly obovate in shape with apices usually rounded to flat and sometimes notched with one or more notches.

NEWLY OPENED FLOWER

The undersurface of the outer, intermediate and inner petals is between 55D and 56A with a small basal attachment zone of between 2D and 4D. The upper surface of the outer, intermediate and inner petals is between 49D and 56B with a small basal attachment zone of between 2D and 4D.

The general tonality of the newly opened flower is between 49D and 56B.

THREE-DAY-OLD FLOWER

The undersurface of the outer and inner petals is between 56b and 56D. The upper surface of the outer and inner petals is between 49D and 56D.

The general tonality of the three-day-old flower is between 49D and 56D.

On the spent bloom, the petals usually drop off cleanly but can sometimes persist, fading to between 56D and 159D, and are not particularly affected by cold, hot, wet, or dry weather.

In October in Upland, Calif., flowers on the bush growing in the garden generally last from four to five or more days. Cut roses grown outdoors and kept at normal indoor living temperatures generally last from four to five days.

MALE REPRODUCTIVE ORGANS

Stamens are few to average in number and are arranged irregularly about the pistils; several are mixed with petaloids. The filaments are of moderately short to medium length, many with anthers. The anthers are medium in size for the class and all open approximately at the same time. Anther color is near 14B when immature and near 166B at maturity. Pollen is somewhat sparse and near 8C in color.

FEMALE REPRODUCTIVE ORGANS

Pistils are average to many in number (approximately 70). The styles are moderately even and moderately long, somewhat thin in caliper, and loosely bunched. Stigma and style color is near 2D. Ovaries are mostly all enclosed in the calyx.

Hips have not been observed on this variety when grown in Upland, Calif.

FOLIAGE

The compound leaves are usually comprises of three to five leaflets and are borne abundantly. The leaves are medium in size for the class, very heavy to crisp in texture, and moderately semi-glossy to glossy in finish. The leaflets are somewhat oval to nearly round in shape with somewhat acute apices and moderately round bases. Their margins are somewhat irregularly dentate. Foliage size is considered medium for the class with a full leaf nominally measuring about 9 to 10 cm in length and about 5 to 6 cm across at the widest point. Individual leaflets are nominally about 2.5 to 3.5 cm long and about 2.5 to 3 cm wide at their widest point. Stem length is considered short to medium ranging nominally from about 12 to 18 cm.

The upper surface of the mature leaf is between 147A and 139A. The undersurface of the mature leaf is between 147C and 191B. The upper surface of the young leaf is between 146A and 144A, sometimes heavily suffused, especially near the edge, with near 183A. The undersurface of the young leaf is between 147C and 138B, sometimes lightly suffused with near 183B.

The rachis is somewhat light to average in caliper and very smooth with very few hairs and stipitate glands on the edge of the upper side. The underside of the rachis is very smooth with very few stipitate glands.

The stipules are moderately short to medium in length with very narrow moderately long points that may turn out at an angle of less than 45 degrees.

The plant displays an above-average degree of resistance to powdery mildew, blackspot and rust as compared to other commercial varieties grown under comparable conditions in Upland, Calif.

GROWTH

The plant has a dwarf, bushy compact, low to medium height habit with very full branching. It displays moderately vigorous growth and the canes are of medium caliper for the class. Plant height and spread is considered to be dwarf, bushy, and compacted. Nominal mature height measurement in California is about 65 to 75 cm and spread in Califorina is nominally about 75 to 90 cm.

The color of the major stems is between 144C and 152D. They bear a few large prickles which are moderately long for the class. The large prickles are almost straight, moderately short to medium length and somewhat narrow based prickle color is near 165B.

The major stem bears no small prickles or fine hairs. The color of the branches is between 144A and 138A. They bear several large prickles which are moderately long for the class. The prickles are almost straight with a moderately short to medium length somewhat narrow base; prickle color is near 162C. The branches bear few small prickles of similar shape and coloration.

The color of the new shoots is between 144A and 146B, sometimes lightly suffused with near 183A. They bear several large prickles which are moderately long for the class. The large prickles are almost straight with a moderately short to medium somewhat narrow base; prickle color is near 180C. The shoots bear few small prickles of similar shape and coloration.

I claim:

1. A new and distinct variety of shrub rose plant substantially as described and illustrated herein.

* * * * *

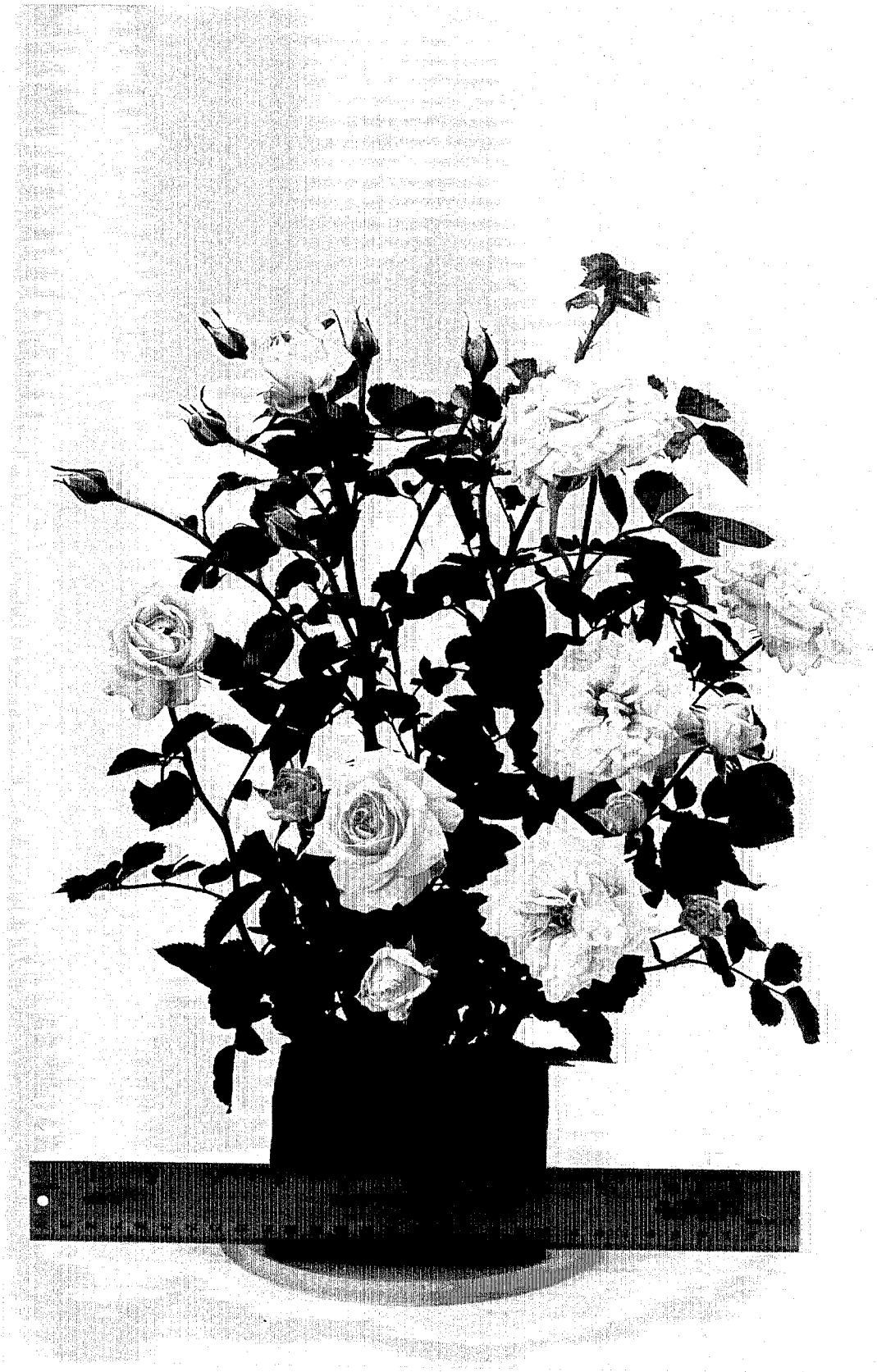

UNITED STATES PATENT AND TRADEMARK OFFICE

CERTIFICATE OF CORRECTION

PATENT NO. : Plant 9,062

DATED : February 28, 1995

INVENTOR(S) : Mogens Olesen; Pernille Olesen

It is certified that error appears in the above-indentified patent and that said Letters Patent is hereby corrected as shown below:

Column 1, line 13, change "availabel" to -- available --.

Column 1, line 22, change "hte" to -- the --.

Column 1, line 41, change "characteristic" to -- characteristics --.

Column 4, line 7, change "comprises" to -- comprised --.

Signed and Sealed this

Fifth Day of September, 1995

*Attest:*

*Attesting Officer*

BRUCE LEHMAN

*Commissioner of Patents and Trademarks*